(12) United States Patent     (10) Patent No.:   US 12,679,529 B2

Smith et al.     (45) Date of Patent:     Jul. 14, 2026

(54) ENERGY RECOVERY DURING CARBON CAPTURE IN PREFORM PRODUCTION PROCESS

(71) Applicant: GOODRICH CORPORATION, Charlotte, NC (US)

(72) Inventors: Kenneth D. Smith, East Longmeadow, MA (US); Sean C. Emerson, Broad Brook, CT (US); Haralambos Cordatos, Colchester, CT (US); Ying She, Rocky Hill, CT (US)

(73) Assignee: GOODRICH CORPORATION, Charlotte, NC (US)

( * ) Notice: Subject to any disclaimer, the term of this patent is extended or adjusted under 35 U.S.C. 154(b) by 79 days.

(21) Appl. No.: 18/477,283

(22) Filed: Sep. 28, 2023

(65) Prior Publication Data

US 2025/0108913 A1     Apr. 3, 2025

(51) Int. Cl.
    *B64C 25/42*     (2006.01)
    *B01D 53/62*     (2006.01)
    (Continued)

(52) U.S. Cl.
    CPC ............ *B64C 25/423* (2013.01); *B01D 53/62* (2013.01); *B01D 53/76* (2013.01); *C07C 1/12* (2013.01); *B01D 2257/504* (2013.01)

(58) Field of Classification Search
    CPC ...... B64C 25/423; B01D 53/62; B01D 53/76; B01D 2257/504; C07C 1/12; C04B 2235/3821; C04B 35/6267; C04B 35/80;

C04B 2235/5212; C04B 2235/5248; C04B 2235/5436; C04B 2235/614; C04B 2235/616; C04B 35/83; C10L 2290/02;

(Continued)

(56) References Cited

U.S. PATENT DOCUMENTS

| | | |
|---|---|---|
| 3,642,460 A | 2/1972 | Thompson |
| 5,128,003 A | 7/1992 | Murdoch et al. |

(Continued)

FOREIGN PATENT DOCUMENTS

| | | |
|---|---|---|
| CN | 116625130 | 8/2023 |
| DE | 102013002583 | 8/2014 |

(Continued)

OTHER PUBLICATIONS

European Patent Office, European Search Report dated Jan. 31, 2025 in Application No. 24201207.8.

(Continued)

*Primary Examiner* — Hoang M Nguyen
(74) *Attorney, Agent, or Firm* — SNELL & WILMER L.L.P.

(57) ABSTRACT

A system is provided for energy recovery. The system includes a heat recovery unit. The heat recovery unit is configured to receive at least one of heat or steam from a methanization reactor operating to convert carbon dioxide ($CO_2$) and supplied hydrogen ($H_2$) via methanization to produce methane ($CH_4$), generate energy using at least one of the heat or the steam from the methanization reactor, and supply the generated energy to at least one of a carbon/ carbon (C/C) preform production process, a separator, or another system.

18 Claims, 7 Drawing Sheets

(51) Int. Cl.
　　　 *B01D 53/76* 　　　 (2006.01)
　　　 *C07C 1/12* 　　　 (2006.01)

(58) Field of Classification Search
　　　 CPC ............. C10L 2290/06; C10L 2290/10; C10L
　　　　　　　　　　　　 2290/541; C10L 2290/542; C10L
　　　　　　　　　　 2290/548; C10L 2290/562; C10L 3/08;
　　　　　　　　　　　　　　　　　　　　　　　 F16D 69/023
　　　 See application file for complete search history.

(56) 　　　　　　　　　 References Cited

U.S. PATENT DOCUMENTS

| | | | | |
|---|---|---|---|---|
| 5,505,824 | A * | 4/1996 | McElroy ................... | C25B 1/04 |
| | | | | 204/266 |
| 5,876,488 | A | 3/1999 | Birbara et al. | |
| 6,255,234 | B1 * | 7/2001 | Erdemir .................. | F16C 33/16 |
| | | | | 442/140 |
| 6,537,470 | B1 * | 3/2003 | Wood ....................... | B29C 70/48 |
| | | | | 264/29.7 |
| 8,034,321 | B2 | 10/2011 | Mauthner et al. | |
| 10,227,901 | B2 | 3/2019 | Bergins et al. | |
| 10,385,732 | B2 * | 8/2019 | Fleischer ............... | B01D 53/22 |
| 10,639,586 | B2 | 5/2020 | Davidian et al. | |
| 11,390,521 | B2 | 7/2022 | Lewis | |
| 11,471,832 | B1 | 10/2022 | Smith et al. | |
| 2011/0120138 | A1 | 5/2011 | Gaiffi et al. | |
| 2015/0045458 | A1 | 2/2015 | Zhang et al. | |
| 2016/0153316 | A1 | 6/2016 | Bergins et al. | |
| 2017/0101196 | A1 | 4/2017 | Karavolos | |
| 2017/0102043 | A1 * | 4/2017 | Opalka ................. | F16D 65/128 |
| 2017/0145330 | A1 | 5/2017 | Kemmet | |
| 2018/0230010 | A1 | 8/2018 | King | |
| 2022/0347612 | A1 | 11/2022 | Atkins et al. | |
| 2023/0028680 | A1 | 1/2023 | Hariri et al. | |
| 2023/0064109 | A1 * | 3/2023 | Lourenco ............ | H01M 8/0668 |
| 2023/0243301 | A1 | 8/2023 | Escobal et al. | |
| 2023/0348788 | A1 | 11/2023 | Shah et al. | |
| 2024/0368773 | A1 * | 11/2024 | Zhu ........................... | C25B 1/04 |

FOREIGN PATENT DOCUMENTS

| | | |
|---|---|---|
| DE | 102016005418 | 11/2017 |
| EP | 3530640 | 3/2023 |
| JP | 2005221150 | 8/2005 |
| JP | 5487483 | 5/2014 |
| KR | 1421187 | 7/2014 |
| WO | 2019000623 | 1/2019 |
| WO | 2020241343 | 12/2020 |
| WO | 2021246318 | 12/2021 |
| WO | 2023203157 | 10/2023 |

OTHER PUBLICATIONS

Hintze et al., "Sabatier Subsystem Thermal Management" NASA Presentation Aug. 21, 2018; https://tfaws.nasa.gov/wp-content/uploads/5_ISRU-Sabatier-Reactor-for-TFAWS-2018.pdf, 9 pages.

Collins Aerospace, "Shaping the future of life support in space", https://www.collinsaerospace.com/what-we-do/Industries/space/crewed-missions, [retrieved Aug. 4, 2023], 11 pages.

Ping Yu, et al., "Poisoning Evaluation of On-Orbit Sabatier Assembly", 2020 International Conference on Environmental Systems, On-line; Paper ICES-2020-378, Jul. 31, 2020, 12 pages.

Yu, et al. "Poisoning Evaluation of On-Orbit Sabatier Assembly" In 2020 International Conference on Environmental Systems, On-line; dated Jul. 31, 2020, Paper ICES-2020-378.

European Patent Office, European Search Report dated Mar. 3, 2025 in Application No. 24203342.1.

European Patent Office, European Search Report dated Apr. 30, 2025 in Application No. 24218434.9.

European Patent Office, European Search Report dated Apr. 30, 2025 in Application No. 24217921.6.

European Patent Office, European Office Action dated Oct. 31, 2025 in Application No. 24201207.8.

European Patent Office, European Office Action dated Jan. 5, 2026 in Application No. 24203342.1.

European Patent Office, European Office Action dated Feb. 11, 2026 in Application No. 24217921.6.

European Patent Office, European Office Action dated Mar. 6, 2026 in Application No. 24218434.9.

USPTO; Requirement for Restriction dated Apr. 22, 2026 in U.S. Appl. No. 18/402,522.

* cited by examiner

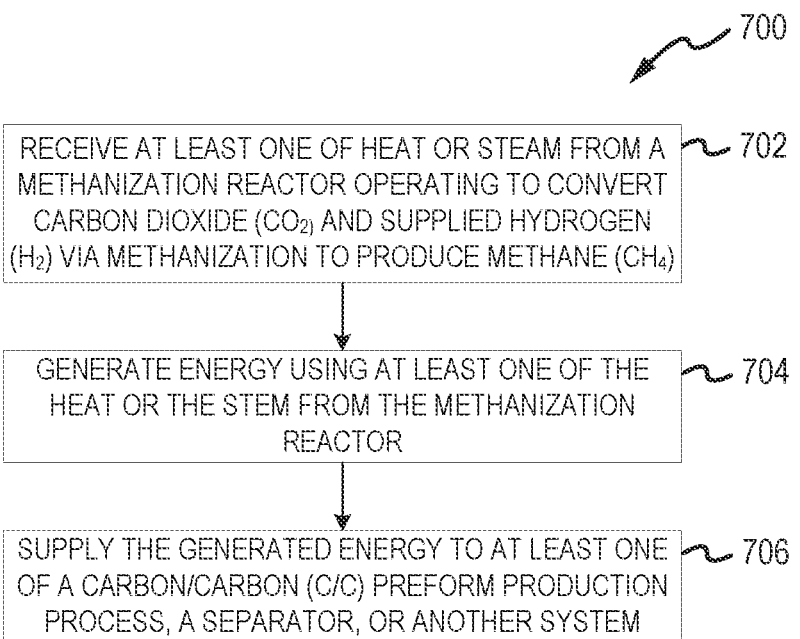

700

RECEIVE AT LEAST ONE OF HEAT OR STEAM FROM A ~ 702
METHANIZATION REACTOR OPERATING TO CONVERT
CARBON DIOXIDE ($CO_2$) AND SUPPLIED HYDROGEN
($H_2$) VIA METHANIZATION TO PRODUCE METHANE ($CH_4$)

GENERATE ENERGY USING AT LEAST ONE OF THE ~ 704
HEAT OR THE STEM FROM THE METHANIZATION
REACTOR

SUPPLY THE GENERATED ENERGY TO AT LEAST ONE ~ 706
OF A CARBON/CARBON (C/C) PREFORM PRODUCTION
PROCESS, A SEPARATOR, OR ANOTHER SYSTEM

FIG. 7

ENERGY RECOVERY DURING CARBON CAPTURE IN PREFORM PRODUCTION PROCESS

FIELD

The present disclosure relates generally to carbon dioxide ($CO_2$) emission recovery, and more particularly, energy recovery in a preform production process.

BACKGROUND

Composite bodies are utilized in various industries, including the aerospace industry. The composite bodies start with a preform that is formed using layers of textile material. Aircraft C/C brake manufacturing is one point source of carbon dioxide ($CO_2$) emissions. Other point sources of $CO_2$ emissions may include thermal protections systems and shaped composite bodies, among others. In such manufacturing, sustainability goals may be to decarbonize operations by a predetermined percentage by a future date. However, capturing $CO_2$ emissions is not only expensive but also problematic to store. This is especially true for $CO_2$ emission sources that do not generate enough $CO_2$ emissions to justify use of a pipeline for underground sequestration.

SUMMARY

According to various embodiments of the present disclosure, a system for energy recovery is provided. The system includes a heat recovery unit. The heat recovery unit is configured to receive at least one of heat or steam from a methanization reactor operating to convert carbon dioxide ($CO_2$) and supplied hydrogen ($H_2$) via methanization to produce methane ($CH_4$), generate energy using at least one of the heat or the steam from the methanization reactor, and supply the energy to at least one of a carbon/carbon (C/C) preform production process, a separator, or another system.

In various embodiments, the system further includes a heat transfer fluid. In various embodiments, the heat recovery unit uses at least one of the heat or the steam to heat the heat transfer fluid. In various embodiments, the heat transfer fluid transfers heat to at least one of the C/C preform production process or the separator. In various embodiments, the system further includes the C/C preform production process. In various embodiments, the C/C preform production process is configured to utilize the heat to produce an aircraft brake and, in the process, generate various off gases from which the supplied $H_2$ is separated. In various embodiments, the system further includes the separator. In various embodiments, the separator is configured to utilize the heat to separate the $CO_2$ from byproducts received from a burner/steam generator and provide the $CO_2$ to the methanization reactor. In various embodiments, the separator is further configured to separate nitrogen ($N_2$) from the byproducts and release the $N_2$ into an atmosphere. In various embodiments, the separator is further configured to separate water ($H_2O$) from the byproducts and feeds the $H_2O$ into the burner/steam generator.

In various embodiments, the heat recovery unit uses the steam to transfer heat to at least one of the C/C preform production process or the separator. In various embodiments, the system further includes a turbine. In various embodiments, the heat recovery unit uses the at least one of the heat or the steam to operate the turbine to produce electricity. In various embodiments, the electricity is either utilized to generate heat in at least one of the C/C preform production process, the separator, or the other system or utilized as direct power for operations to power equipment or processes.

In various embodiments, the system further includes a burner/steam generator. In various embodiments, in generating the energy using the steam from the methanization reactor, the heat recovery unit is configured to condense excess steam to water ($H_2O$) which is supplied to the burner/steam generator. In various embodiments, the system further includes a burner/steam generator and a condenser. In various embodiments, in generating the energy using the steam from the methanization reactor, the heat recovery unit provides excess steam to the condenser. In various embodiments, the condenser is configured to condense the steam to water ($H_2O$) which is supplied to the burner/steam generator.

Also disclosed herein is a method for energy recovery. The method includes receiving, by a heat recovery unit, at least one of heat or steam from a methanization reactor operating to convert carbon dioxide ($CO_2$) and supplied hydrogen ($H_2$) via methanization to produce methane ($CH_4$), generating, by the heat recovery unit, energy using at least one of the heat or the steam from the methanization reactor, and supplying, by the heat recovery unit, the energy to at least one of a carbon/carbon (C/C) preform production process, a separator, or another system.

In various embodiments, the heat recovery unit uses at least one of the heat or the steam to heat a heat transfer fluid. In various embodiments, the heat transfer fluid transfers heat to at least one of the C/C preform production process or the separator. In various embodiments, the C/C preform production process is configured to utilize the heat to produce an aircraft brake and, in the process, generate various off gases from which the supplied $H_2$ is separated. In various embodiments, the separator is configured to utilize the heat to separate the $CO_2$ from byproducts received from a burner/steam generator and provide the $CO_2$ to the methanization reactor. In various embodiments, the separator is further configured to separate nitrogen ($N_2$) from the byproducts and release the $N_2$ into an atmosphere. In various embodiments, the separator is further configured to separate water ($H_2O$) from the byproducts and feeds the $H_2O$ into the burner/steam generator.

In various embodiments, the heat recovery unit uses the steam to transfer heat to at least one of the C/C preform production process or the separator. In various embodiments, the heat recovery unit uses the at least one of the heat or the steam to operate a turbine to produce electricity. In various embodiments, the electricity is either utilized to generate heat in at least one of the C/C preform production process, the separator, or the other system or utilized as direct power for operations to power equipment or processes. In various embodiments, in generating the energy using the steam from the methanization reactor, the heat recovery unit is configured to condense excess steam to water ($H_2O$) which is supplied to a burner/steam generator. In various embodiments, in generating the energy using the steam from the methanization reactor, the heat recovery unit provides excess steam to a condenser. In various embodiments, the condenser is configured to condense the steam to water ($H_2O$) which is supplied to a burner/steam generator.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

FIG. 7 illustrates a method for energy recovery of converting recovered $CO_2$ into other products, in accordance with various embodiments.

DETAILED DESCRIPTION

Figure 1A:
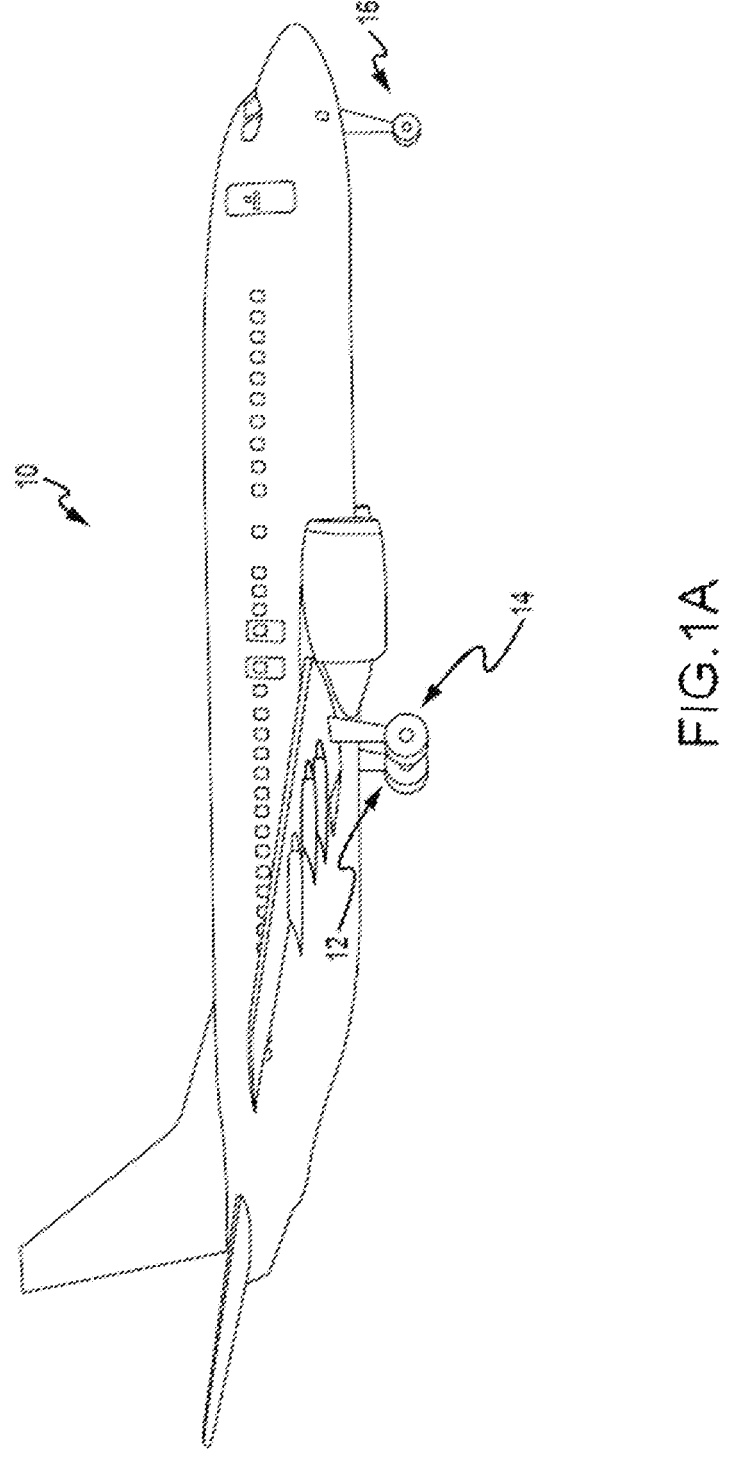
FIG. 1A illustrates an exemplary aircraft having a brake system, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an," or "the" may include one or more than one and that reference to an item in the singular may also include the item in the plural. Further, all ranges may include upper and lower values and all ranges and ratio limits disclosed herein may be combined.

In some typical carbon/carbon (C/C) preform production process, such as aircraft C/C brake manufacturing, thermal protections systems, and shaped composite bodies, among others, carbon dioxide ($CO_2$) emissions account for a substantial percentage of a total $CO_2$ emissions for some corporations. In such corporations, sustainability goals may be to decarbonize operations by a predetermined percentage by a future date. While technology for capturing $CO_2$ emissions may be well-established and already in practice for applications ranging from enhanced oil recovery to carbonation of soft drinks, one of the costs associated with capturing $CO_2$ emissions is the logistics and additional energy input associated with $CO_2$ emission sequestration, which, for large point sources such as power plants, involves pressurization and transfer via pipeline to underground storage locations. Such $CO_2$ emission recovery is unlikely to become a viable solution for relatively small $CO_2$ emission point sources.

Disclosed herein are systems and methods for energy recovery of converting recovered $CO_2$ into other products. Accordingly, in various embodiments, in manufacturing processes where other gases such as hydrogen ($H_2$) are also generated as a byproduct, the $H_2$ may react catalytically with the recovered $CO_2$ to form methane ($CH_4$) via a methanization reaction, i.e., the main species in natural gas:

$$CO_2+4H_2 \rightarrow CH_4+2H_2O$$

This methanization reaction may also be referred to as a Sabatier reaction. In manufacturing processes, such as preform forming manufacturing, the methanization reaction offers the most straightforward path for management of $CO_2$ emissions, given that the preform forming manufacturing process already typically utilizes methane (natural gas) for operation and given that the C/C brake manufacturing process generates excess $H_2$. While the excess $H_2$ generated by the C/C brake manufacturing process may not be enough to account for the entire $CO_2$ emissions, the $H_2$ may be supplemented with additional "green hydrogen" (i.e., produced sustainably), which is projected to become widely available. Additionally, in various embodiments, heat generated during the methanization reaction as well as any steam ($H_2O$) produced from the methanization reactor may also be utilized on a bottoming cycle, where waste heat and steam generated during the $CO_2$ capture process is used for indirect heat and/or electric heat, which may be utilized in the manufacturing processes. That is, in various embodiments, enthalpy of the reaction from the methanization reactor is approximately −165.4 kilojoules per mole (kJ/mol), i.e. a loss of energy due to an exothermic reaction, which provides a significant energy stream for thermal recovery.

Referring now to FIG. 1A, in accordance with various embodiments, an aircraft 10 is illustrated. The aircraft 10 includes landing gear, which may include a left main landing gear 12, a right main landing gear 14, and a nose landing gear 16. The landing gear support the aircraft 10 when it is not flying, allowing the aircraft 10 to taxi, take off, and land without damage. While the disclosure refers to the three landing gear configurations just described, the disclosure nevertheless contemplates any number of landing gear configurations.

Figure 1B:
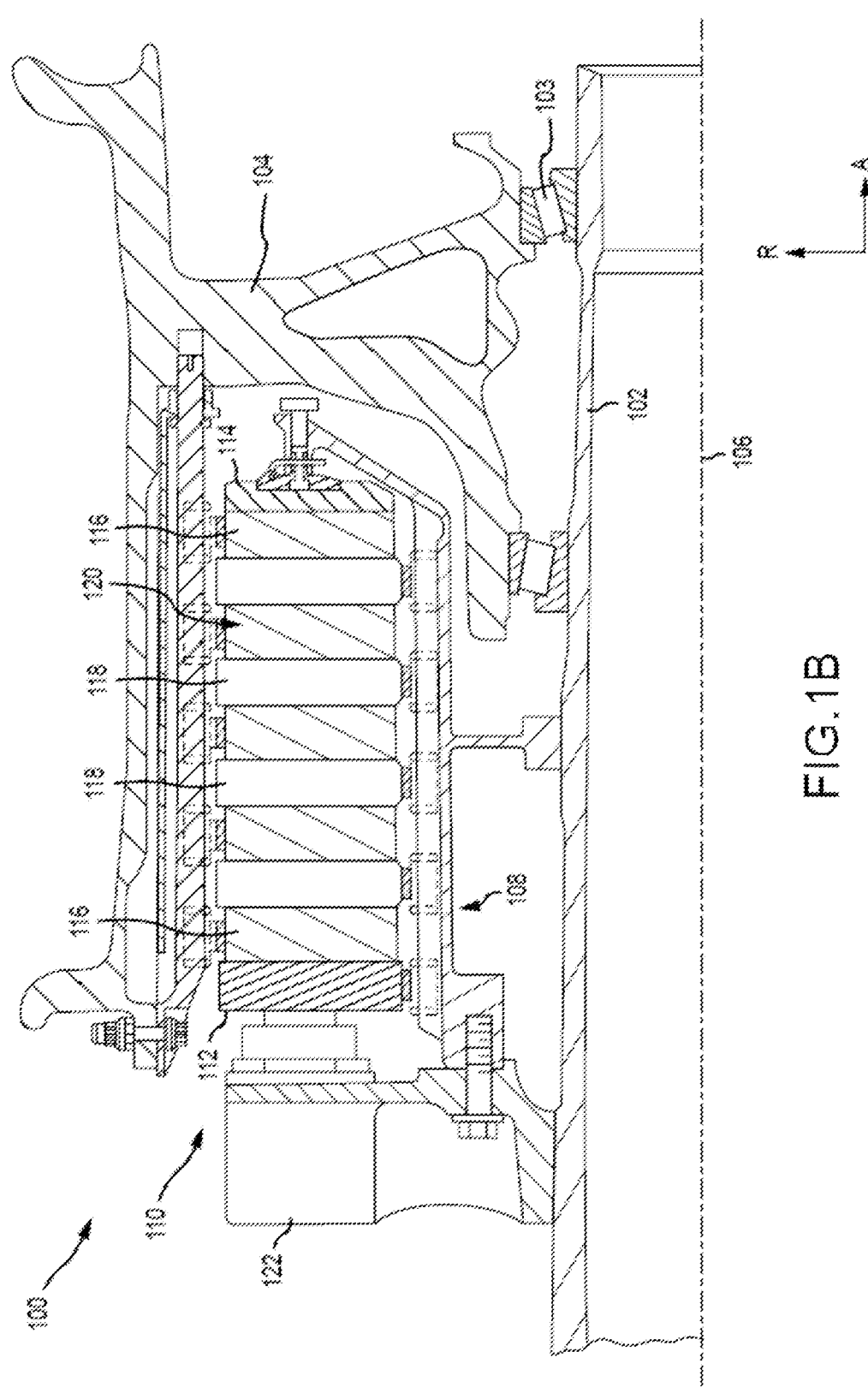
FIG. 1B illustrates a cross-sectional view of a brake assembly, in accordance with various embodiments.

Referring now to FIG. 1B, in accordance with various embodiments, a schematically depicted a brake mechanism 100 is illustrated configured for use on a landing gear, such as, for example, each of the left main landing gear 12 and the right main landing gear 14 described above with reference to FIG. 1A. In various embodiments, the brake mechanism 100 is mounted on an axle 102 for use with a wheel 104 disposed on and configured to rotate about the axle 102 via one or more bearing assemblies 103. A central axis 106 extends through the axle 102 and defines a center of rotation of the wheel 104. As used herein, the term "radial" refers to directions perpendicular to a central axis 106 of fibrous preform, the term "axial" refers to direction parallel to central axis 106, and the term "circumferential" reference to directions about central axis 106. A torque plate barrel 108 (sometimes referred to as a torque tube or a torque plate) is aligned concentrically with the central axis 106, and the wheel 104 is rotatable relative to the torque plate barrel 108.

The brake mechanism 100 includes a piston assembly 110, a pressure plate 112 disposed adjacent the piston assembly 110, an end plate 114 positioned a distal location from the piston assembly 110, and a plurality of rotor disks 116 interleaved with a plurality of stator disks 118 positioned intermediate the pressure plate 112 and the end plate 114. The pressure plate 112, the plurality of rotor disks 116, the plurality of stator disks 118, and the end plate 114 together form a brake heat sink or brake stack 120. The pressure plate 112, the end plate 114, and the plurality of stator disks 118 are mounted to the torque plate barrel 108 and remain rotationally stationary relative to the axle 102. The plurality of rotor disks 116 is mounted to the wheel 104 and rotate with respect to each of the pressure plate 112, the end plate 114, and the plurality of stator disks 118.

An actuating mechanism for the brake mechanism 100 includes a plurality of piston assemblies, including the piston assembly 110, circumferentially spaced around a piston housing 122 (only one piston assembly is illustrated in FIG. 1B). Upon actuation, the plurality of piston assemblies affects a braking action by urging the pressure plate 112 and the plurality of stator disks 118 into frictional engagement with the plurality of rotor disks 116 and against the end plate 114. Through compression of the plurality of rotor disks 116 and the plurality of stator disks 118 between the pressure plate 112 and the end plate 114, the resulting frictional contact slows or stops or otherwise prevents rotation of the wheel 104. In various embodiments, the brake disks of brake mechanism 100 (e.g., rotor disks 116 and the stator disks 118) are fabricated from various composite materials, such as, for example, carbon/carbon (C/C) composite or ceramic matrix composite (CMCs), that enable the brake disks to withstand and dissipate the heat generated during and following a braking action.

In accordance with various embodiments, rotor disks 116 and/or stator disks 118 are each comprised of a carbon-carbon (C/C) material having a high specific heat particulate interspersed throughout the rotor disks 116 and/or stator disks 118, where high specific heat particulate includes any particulate or powder (typically ceramic) that raises the specific heat of the disk above that of C/C composite alone. For example, in various embodiments, the rotor disks 116 and/or stator disks 118 may comprise a C/C composite that includes a percentage of boron, a boron component, or other material having a high specific heat (i.e., a specific heat greater than the specific heat of the C/C composite alone). In various embodiments, rotor disks 116 and/or stator disks 118 may comprise a C/C composite with a percentage of boron carbide ($B_4C$) disposed substantially throughout the disk.

In various embodiments, the process of interspersing the boron carbide (or other high specific heat component) into the C/C composite is performed by a slurry infiltration process. As described in further detail below, the slurry may infiltrate a fiber preform employed to form the C/C composite in the radial, or in-plane, direction. The slurry may infiltrate via through thickness infiltration of the carbonize preforms. In various embodiments infiltrating in the radial, as opposed to the axial, direction may allow greater volumes and/or larger size particles to be infiltrated. Increasing the volume and/or size of the particles may facilitate the densification process by increasing the surface area available for the matrix material to bond to and by decreasing the open, or empty, volume within the preform. In-plane infiltration may also allow thicker fibrous preforms (e.g., fibrous preforms including a greater number of fiber layers) to be used in the manufacture rotor disks 116 and/or stator disks 118, as the compared to axial infiltration.

Figure 2:
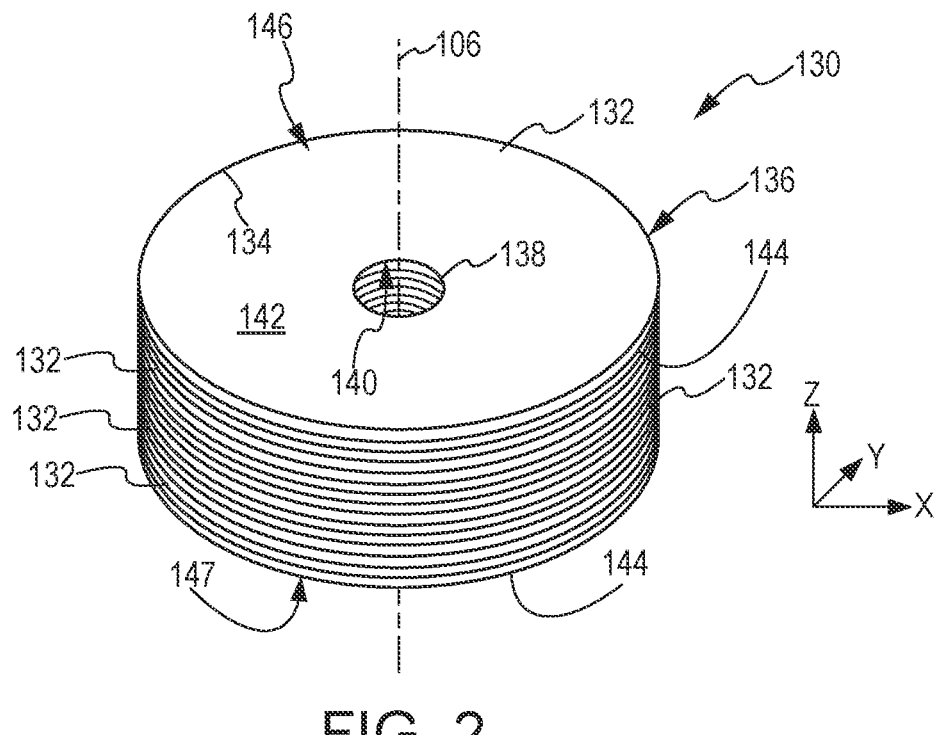
FIG. 2 illustrates a fibrous preform, in accordance with various embodiments.

Referring now to FIG. 2, in accordance with various embodiments, a fibrous preform 130 is illustrated. Fibrous preform 130 may be employed to form a rotor disk 116 or a stator disk 118, as described above. Fibrous preform 130 may comprise a porous structure comprised of a plurality of stacked textile layers 132. Each textile layer 132 having a thickness in a first dimension (i.e., the Z-direction) that may be substantially less than a thickness of the layer 132 in the other two dimensions (i.e., the X-direction and the Y-direction). As used herein, the "in-plane" direction refers to directions parallel to the thicker two dimensions (i.e., parallel to the X and Y directions and perpendicular to the Z-direction).

A porous structure may comprise any structure derived from a fibrous material such as carbon fibers or the like. In various embodiments, the carbon fibers may be derived from polyacrylonitrile (PAN), rayon (synthetic fiber derived from cellulose), oxidized polyacrylonitrile fiber (OPF), pitch, or the like. The starting fiber may be pre-oxidized PAN or fully carbonized commercial carbon fiber. Fibrous preform 130 may be prepared by needling the textile layers 132 of fibrous preform 130. Needling the textile layers 132 of fibrous preform 130 tends to push fibers from one layer 132 to the next layer 132, thereby forming z-fibers that extend axially across the layers 132. Needling pulls fibers from the in-plane direction and forces the fibers into the z-fiber direction. After needling, fibrous preform 130 may comprise fibers extending in three different directions: the radial direction, the circumferential direction, and the axial direction (or the X, Y, and Z directions).

Fibrous preform 130 may be fabricated using a net shape preforming technology or may be cut from a needled board. Fibrous preform 130 may be a lay-up of woven, braided or knitted textile layers 132. The fibrous material may be in the form of chopped carbon fibers molded to form layers 132. Prior to the densification process, the fibrous material may be formed into a preform having any desired shape or form. For example, the fibrous preform may be in the form of a disk having any shape such as, for example, a polygon, a cylinder, a triangle, annular, square, rectangle, pentagon, hexagon, octagon, or the like. In various embodiments, layers 132 and fibrous preform 130 may have a generally annular shape. In accordance with various embodiments, the outer circumferential (or outer perimeter) surfaces 134 of layers 132 may form an outer diameter (OD) 136 of fibrous preform 130, and the inner circumferential (or inner perimeter) surfaces 138 of layers 132 may form an inner diameter (ID) 140 of fibrous preform 130. Each layer 132 includes a first axial face 142 and a second axial face 144 opposite the first axial face 142. First and second axial faces 142, 144 extend from outer circumferential surface 134 to inner circumferential surface 138. Layers 132 are stacked such that the first axial face 142 of one layer 132 is oriented toward the second axial face 144 of the adjacent layer 132. First axial face 142 of the uppermost layer 132 forms the upper axial end 146 of fibrous preform 130 and the second axial face 144 of the bottommost layer 132 forms the lower axial end 147 of fibrous preform 130 (i.e., the two layers 132 that are farther apart from one another in the axial direction form the axial ends 146, 147 of the fibrous preform).

Figure 3:
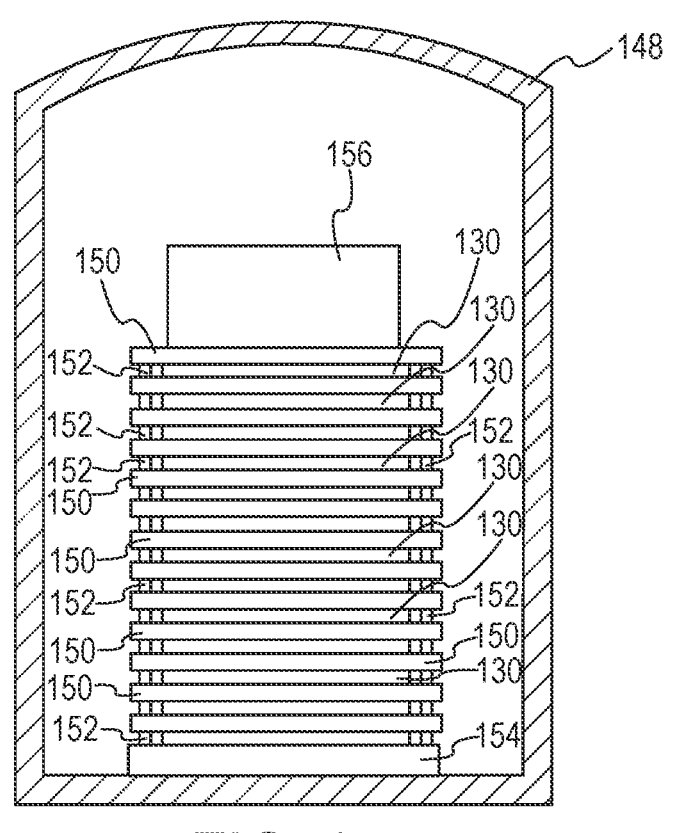
FIG. 3 illustrates a fibrous preform in a carbonization furnace, in accordance with various embodiments.

As shown in FIG. 3, in accordance with various embodiments, fibrous preforms 130 being placed in a furnace 148 for carbonization is illustrated. The carbonization process may be employed to convert the fibers of the fibrous preforms 130 into pure carbon fibers, as used herein only "pure carbon fibers" means carbon fibers comprised of at least 99% carbon. The carbonization process is distinguished from the densification process described below in that the densification process involves infiltrating the pores of the fibrous preform 130 and depositing a matrix (e.g., carbon, phenolic resin, or any other desired matrix material) within and around the carbon fibers of the fibrous preform, and the carbonization process refers to the process of converting the fibers of the fibrous preform 130 into pure carbon fibers.

In various embodiments, a plurality of fibrous preforms 130 may be placed on top of one another with separator plates 150 and spacing stops 152 disposed between adjacent fibrous preforms 130. For example, the bottommost fibrous preform 130 may be placed on a base plate 154 at the bottom of carbonization furnace 148. A separator plate 150 may be placed on top of the bottommost fibrous preform 130. Another fibrous preform 130 may then be placed on the separator plate 150, and another separator plate 150 may be placed on that fibrous preform 130. A stack of fibrous preforms 130 and separator plates 150 may be constructed in this manner, with each fibrous preform 130 being separated from superjacent and subjacent fibrous preforms 130 by separator plates 150. Stops 152 may be placed between each of the separator plates 150. The stops 152 may comprise a height that is less than the thickness of the fibrous preform 130 prior to carbonization. Stops 152 may define a target thickness of the fibrous preform 130 after carbonization. In that regard, after the stack of fibrous preforms 130 is constructed, and before the carbonization process has started, gaps may exist between the stops 152 and adjacent separator plates 150. During carbonization, a compressive load may be applied to the fibrous preforms 130, thereby compressing the fibrous preforms 130 until stops 152 contact adjacent separator plates 150.

In various embodiments, compressive pressure may be applied to fibrous preforms 130 during the carbonization. The compressive pressure may be applied by placing a weight 156 over fibrous preforms 130, or by applying a compressive load to the fibrous preforms 130 by other suitable means. The compressive pressure may be applied along the direction of the z-fibers. It will be appreciated by those skilled in the art that the mass of weight 156 and/or the compressive force generated by weight 156 may vary depending on the size of fibrous preforms 130, the pre-carbonization fiber volume of fibrous preforms 130, the desired post-carbonization fiber volume of fibrous preforms 130, and/or the number fibrous preforms 130 being compressed. As used herein, "fiber volume" refers the percentage of the total volume of the fibrous preform that is formed by the fibers of the fibrous preform. For example, a fiber volume of 18% means the fibers of the fibrous preform form 18% of the total volume of fibrous preform. In various embodiments, after carbonization, fibrous preform 130 includes a fiber volume of between 10% and 50%. In various embodiments, after carbonization, fibrous preform 130 includes a fiber volume of between 15% and 25%. In various embodiments, fibrous preforms 130 having a low fiber volume may be desirable for the infiltration methods disclosed herein. In various embodiments, after carbonization, fibrous preform 130 may comprise a fiber volume of less than 25%. For example, in various embodiments, after carbonization, fibrous preform 130 may comprise a fiber volume of 21% or, in various embodiments, fibrous preform 130 may comprise a fiber volume of 18%.

After carbonization, fibrous preform 130, may be densified using, for example, CVI. In various embodiments, prior to densification, fibrous preform 130 is infiltrated with a slurry including a high specific heat particulate. For example, in various embodiments, fibrous preform 130 is infiltrated with a ceramic slurry (i.e., a slurry comprised of a liquid carrier and ceramic particulates). In various embodiments, the slurry infiltration process includes preparation of a slurry including a ceramic particulate (e.g., an aqueous $B_4C$-based slurry) and immersing the carbonized fibrous preform 130 into the slurry for a period of time sufficient for the particulate (e.g., the $B_4C$) to infiltrate the fibrous preform 130.

The slurry includes sacrificial fibers. For instance, the sacrificial fibers/particulates are mixed into the slurry. The sacrificial fibers may be a polyethylene or polyester fiber such that, in response to heating to carbon CVI temperatures (e.g., 100° F. and 205° F. (38° C. and 96° C.)) will burn. In various embodiments, the preform is heated up to 1000° C. in order to cause the sacrificial fibers for burn away, or decompose. When the sacrificial fibers are burned away, or decompose, channels are formed, thus improving carbon CVI infiltration. For instance, the channels provide a pathway for the CVI to get to in. However, polyester or polyethylene fibers may be too large to incorporate directly into the $B_4C$ slurry. Accordingly, the sacrificial fibers may be injected into the fibrous preform 130. For instance, the sacrificial fibers may be injected using a syringe or other means, prior to completing $B_4C$ slurry infiltration. By injecting using a syringe, the sacrificial fibers may be distributed in the matrix of the boron carbide.

Slurry may include high specific heat particulate and a liquid carrier (such as, for example, water and/or alcohol). In various embodiments, slurry may further include a high specific heat particulate, a binder (e.g., a polymeric adhesive or polyvinyl acetate), and a liquid carrier (e.g., water). It will be appreciated by those skilled in the art that liquid carriers other than water may be used and that the type and/or volume of liquid carrier and/or of binder may be selected based on the composition of the high specific heat particulate. In various embodiments, slurry may be a $B_4C$-based slurry and may be prepared by mixing $B_4C$ powder in water with appropriate additives, such as wetting agents and dispersants. The $B_4C$ powder may comprise particulates having an average particle sizes from sub-micron up to about 30 microns. As used in the previous context only, "about" means±5 microns.

The slurry further includes the sacrificial fibers. The sacrificial fibers are added to the solution of the slurry. In various embodiments, the sacrificial fibers make up 5% of the slurry solution. In various embodiments, the sacrificial fibers make up 10% of the slurry solution. For instance, the sacrificial fibers make up 0.5%-10% of the slurry. The sacrificial fibers may be a micro polyester particle. The slurry solution may be loaded into the syringe. A user may then use the syringe to inject the slurry, including the sacrificial fibers, into the fibrous preform 130. The user may inject the fibrous preform 130 in a plurality of locations. For instance, the user may inject/poke the fibrous preform 130 at ten locations. In various embodiments, a bank of syringes may be provided to operate as an assembly-line system to prepare multiple fibrous preforms may be injected simultaneously with the sacrificial fibers.

Infiltration using a syringe facilitates achieving a uniform distribution of the sacrificial fibers, which in turn improves carbon CVI infiltration once the fibers are burned around during the heat-up to carbon CVI process temperature. By raising the thermal capacity of the material, more energy may be absorbed per unit mass. Accordingly, the brakes may be manufactured smaller, for instance. Further, the friction and wear characteristics may be improved.

Figure 4:
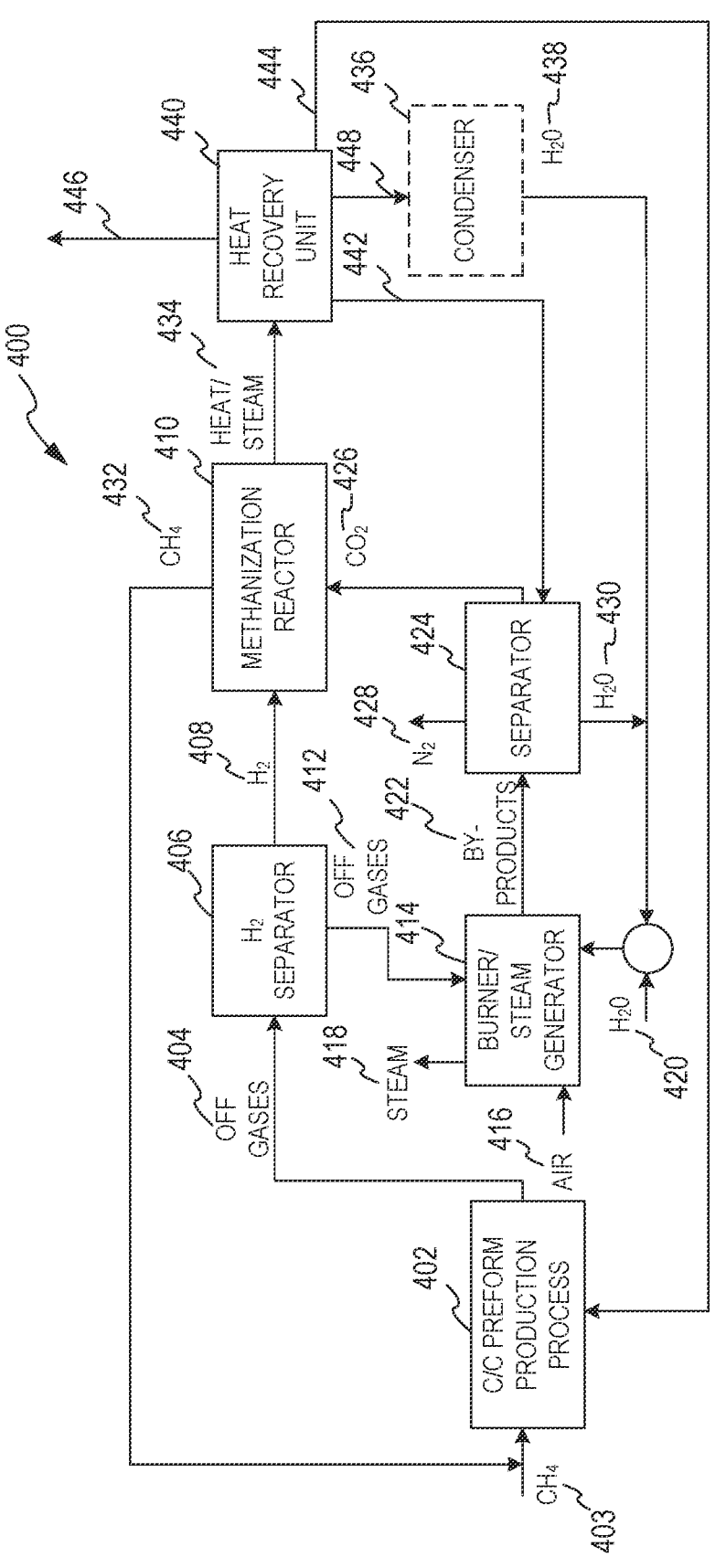
FIG. 4 illustrates a system for energy recovery of converting recovered $CO_2$ into other products, in accordance with various embodiments.

As described previously, the process illustrated and described with respect to FIG. 3 is the emission of off gases that include but are not limited to hydrogen ($H_2$) and carbon dioxide ($CO_2$). Referring now to FIG. 4, in accordance with various embodiments, a system 400 for energy recovery of converting recovered $CO_2$ into other products is illustrated. In various embodiments, the C/C preform production process 402 utilizes natural gas such as methane ($CH_4$) 403 to perform various operations in the production of the aircraft brakes. However, in various embodiments, during the C/C preform production process 402, various off gases 404, i.e. hydrocarbons, are produced. Accordingly, in system 400, the C/C preform production process 402 feeds the various off gases 404, i.e., hydrocarbons, $CO_2$, $H_2$, and nitrogen ($N_2$), among others, into $H_2$ separator 406. In various embodiments, $H_2$ separator 406 separates $H_2$ 408 from the various off gases 404 using one or more of membrane separation, pressure swing absorption (PSA), captured by solid sorbents, or cryogenic distillation, among others. In various embodiments, the $H_2$ separator 406 feeds the $H_2$ 408 into methanization reactor 410 and feeds the remaining off gases 412, i.e. heavier hydrocarbons, as well as $CO_2$ and $N_2$, among others, into burner/steam generator 414.

In various embodiments, the burner/steam generator 414 burns the remaining off gases 412 utilizing air 416 to generate steam 418 from incoming water ($H_2O$) 420. In various embodiments, the steam 418 may be utilized to operate other components of the C/C preform production process 402. During the operations performed by the burner/steam generator 414, in addition to generating the steam 418, the burner/steam generator 414 generates byproducts 422, such as such as $CO_2$, $H_2O$, and $N_2$, among others, which the burner/steam generator 414 feeds into separator 424. Separator 424 may operate to separate the $CO_2$ 426 from the byproducts 422, which is fed into methanization reactor 410, to separate the $N_2$ 428 from the byproducts 422, which may be released into the atmosphere, and to separate the $H_2O$ 430 from the byproducts 422, which may be fed into the burner/steam generator 414 along with $H_2O$ 420. The separator 424 may one or more of absorption, adsorption, cryogenic distillation, captured by solid sorbents or solvents such as mono-ethanol amine (MEA), or membrane separation, among others for the separation process.

In various embodiments, the methanization reactor 410 utilizes the incoming $H_2$ 408 and $CO_2$ 426 to perform a methanization process in order to produce methane ($CH_4$) 432, which is fed into the C/C preform production process 402 or another system to perform various operations in the production the aircraft brakes, such as heat generation. In various embodiments, in the production of $CH_4$ 432, the methanization reactor 410 also produces heat and/or steam 434 in the form of a gas exhaust and/or steam exhaust, which is fed into heat recovery unit 440. In various embodiments, the heat recovery unit 440 may operate to utilize the heat and/or steam 434 to generate energy 442, i.e. heat, via thermal transfer to another fluid that, once heated, may be utilized as a heat transfer fluid. In various embodiments, the heat recovery unit 440 may feed the energy 442, i.e. the heat transfer fluid, via a closed loop process, to separator 424 in order for separator 424 to utilize the provided heat to separate the $CO_2$ 426 from the byproducts 422, which is fed into methanization reactor 410, to separate the $N_2$ 428 from the byproducts 422, which may be released into the atmosphere, and to separate the $H_2O$ 430 from the byproducts 422, which may be fed into the burner/steam generator 414 along with $H_2O$ 420. In various embodiments, the heat recovery unit 440 may operate to utilize the heat and/or steam 434 to generate energy 444, i.e. heat, via thermal transfer to another fluid that, once heated, may be utilized as a heat transfer fluid. In various embodiments, the heat recovery unit 440 may feed the energy 444, i.e. the heat transfer fluid, via a closed loop process, to the C/C preform production process 402 in order that the C/C preform production process 402 uses the heat for performing various operations in the production of the aircraft brakes.

In various embodiments, rather than using the heat and/or steam 434 to heat, via thermal transfer, another fluid, i.e. the heat transfer fluid, in various embodiments, the heat recovery unit 440 may feed the heat and/or steam 434 as energy 442, via a closed loop process, to separator 424 in order for separator 424 to separate the $CO_2$ 426 from the byproducts 422, which is fed into methanization reactor 410, to separate the $N_2$ 428 from the byproducts 422, which may be released into the atmosphere, and to separate the $H_2O$ 430 from the byproducts 422, which may be fed into the burner/steam generator 414 along with $H_2O$ 420. In various embodiments, rather than the heat recovery unit 440 using the heat and/or steam 434 to heat, via thermal transfer, another fluid, i.e. the heat transfer fluid, in various embodiments, the heat recovery unit 440 may feed the heat and/or steam 434 as energy 444, via a closed loop process, to the C/C preform production process 402 for use in performing various operations in the production of the aircraft brakes.

In various embodiments, the heat recovery unit 440 may operate to utilize the heat and/or steam 434 to operate a turbine of an electric generator, thereby producing energy 442, i.e. electricity. In various embodiments, the heat recovery unit 440 may feed the energy 442, i.e. the electricity, to separator 424 in order for separator 424 to utilize the energy 442 to produce electric heat to separate the $CO_2$ 426 from the byproducts 422, which is fed into methanization reactor 410, to separate the $N_2$ 428 from the byproducts 422, which may be released into the atmosphere, and to separate the $H_2O$ 430 from the byproducts 422, which may be fed into the burner/steam generator 414 along with $H_2O$ 420. In various embodiments, the heat recovery unit 440 may operate to utilize the heat and/or steam 434 to operate a turbine of an electric generator, thereby producing energy 444, i.e. electricity. In various embodiments, the heat recovery unit 440 may feed the energy 444, i.e. the electricity, to the C/C preform production process 402 to utilize the energy 442 to produce electric heat in order that the C/C preform production process 402 uses the heat for performing various operations in the production of the aircraft brakes.

In various embodiments, the heat recovery unit 440 using the heat and/or steam 434 to operate a turbine of an electric generator, thereby producing energy 442, 444, i.e. electricity, any excess energy, 446, i.e. electricity, may be fed into other processes within a plant where the C/C preform production process 402 operates or sold as excess energy to an electric provider via an electric grid. In various embodiments, excess steam 448 of the heat and/or steam 434 may then be condensed to generate $H_2O$ 438, which may be fed into the burner/steam generator 414 along with $H_2O$ 420 and $H_2O$ 430. In various embodiments, the condensing may be performed by the heat recovery unit 440 in response the heat recovery unit 440 is able to remove enough heat from the heat and/or steam 434. In various embodiments, in response the heat recovery unit 440 not being able to remove enough heat from the heat and/or steam 434, then the excess steam 448 may be fed to condenser 436. In various embodiments, the condenser 436 condenses the excess steam 448. Accordingly, system 400 provides for $CO_2$ emission recovery by converting the recovered $CO_2$ into other products that may be utilized by the C/C preform production process 402.

Figure 5:
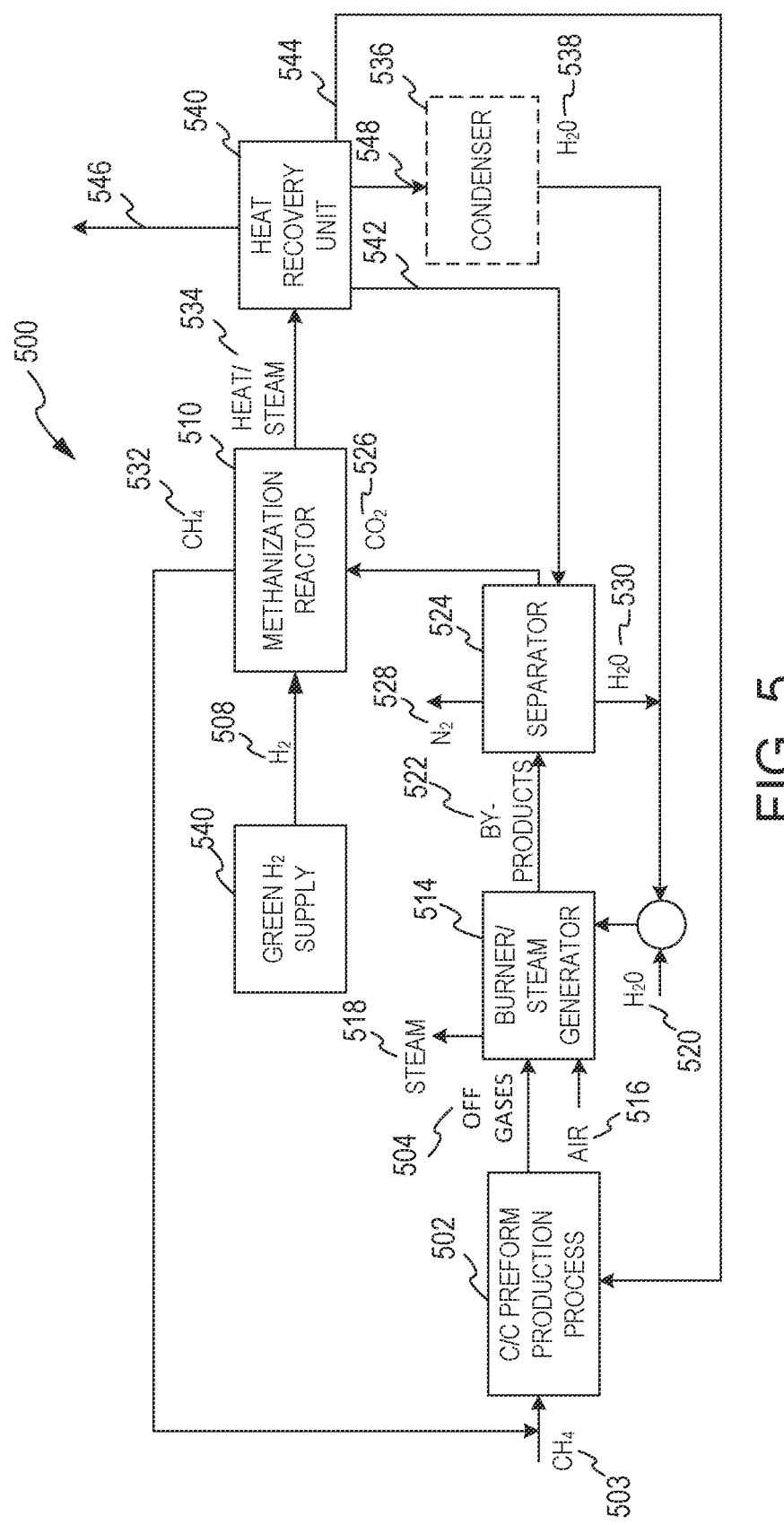
FIG. 5 illustrates a system for energy recovery of converting recovered $CO_2$ into other products, in accordance with various embodiments.

Referring now to FIG. 5, in accordance with various embodiments, a system 500 for energy recovery of converting recovered $CO_2$ into other products is illustrated. In various embodiments, the C/C preform production process

11

502 utilizes natural gases such as methane (CH$_4$) 503 to perform various operation in the production the aircraft brakes. However, in various embodiments, during the C/C preform production process 502 various off gases 504, i.e. hydrocarbons, are produced. Accordingly, in system 500, the C/C preform production process 502 feeds the various off gases 504, i.e., hydrocarbons, CO$_2$, H$_2$, and nitrogen (N$_2$), among others, into burner/steam generator 514. In various embodiments, the burner/steam generator 514 burns the various off gases 504 utilizing air 516 to generate steam 518 from incoming water (H$_2$O) 520. In various embodiments, the steam 518 may be utilized to operate other components of the C/C preform production process 502. During the operations performed by the burner/steam generator 514, in addition to generating the steam 518, the burner/steam generator 514 generates byproducts 522, such as CO$_2$, H$_2$O, and N$_2$, among others, which the burner/steam generator 514 feeds into separator 524. Separator 524 may operate to separate the CO$_2$ 526 from the byproducts 522, which is fed into methanization reactor 510, to separate the N$_2$ 528 from the byproducts 522, which may be released into the atmosphere, and to separate the H$_2$O 530 from the byproducts 522, which may be fed into the burner/steam generator 514 along with H$_2$O 420. The separator 524 may be one or more of absorption, adsorption, cryogenic distillation, captured by solid sorbents or solvents such as mono-ethanol amine (MEA), or membrane separation, among others for the separation process.

In various embodiments, the methanization reactor 510 utilizes the incoming H$_2$ 508 provided via green H$_2$ supply 540 and CO$_2$ 526 to perform a methanization process in order to produce methane (CH$_4$) 532, which is fed into the C/C preform production process 502 or another system to perform various operations in the production the aircraft brakes, such as heat generation. In various embodiments, green H$_2$ supply 540 may be H$_2$ generated sustainably via electrolysis from a green H$_2$ supply device, such as a solar generator or wind generator. In various embodiments, in the production of CH$_4$ 532, the methanization reactor 510 also produces heat and/or steam 534 in the form of a gas exhaust and/or steam exhaust, which is fed into heat recovery unit 540. In various embodiments, the heat recovery unit 540 may operate to utilize the heat and/or steam 534 to generate energy 542, i.e. heat, via thermal transfer, another fluid that, once heated, may be utilized as a heat transfer fluid. In various embodiments, the heat recovery unit 540 may feed the energy 542, i.e. the heat transfer fluid, via a closed loop process, to separator 524 in order for separator 524 to utilize the provided heat to separate the CO$_2$ 526 from the byproducts 522, which is fed into methanization reactor 510, to separate the N$_2$ 528 from the byproducts 522, which may be released into the atmosphere, and to separate the H$_2$O 530 from the byproducts 522, which may be fed into the burner/steam generator 514 along with H$_2$O 520. In various embodiments, the heat recovery unit 540 may operate to utilize the heat and/or steam 534 to generate energy 544, i.e. heat, via thermal transfer, another fluid that, once heated, may be utilized as a heat transfer fluid. In various embodiments, the heat recovery unit 540 may feed the energy 544, i.e. the heat transfer fluid, via a closed loop process, to the C/C preform production process 502 in order that the C/C preform production process 502 uses the heat for performing various operations in the production of the aircraft brakes.

In various embodiments, rather than using the heat and/or steam 534 to heat, via thermal transfer, another fluid, i.e. the heat transfer fluid, in various embodiments, the heat recovery unit 540 may feed the heat and/or steam 534 as energy 542, via a closed loop process, to separator 524 in order for separator 524 to separate the CO$_2$ 526 from the byproducts 522, which is fed into methanization reactor 510, to separate the N$_2$ 528 from the byproducts 522, which may be released into the atmosphere, and to separate the H$_2$O 530 from the byproducts 522, which may be fed into the burner/steam generator 514 along with H$_2$O 520. In various embodiments, rather than the heat recovery unit 540 using the heat and/or steam 534 to heat, via thermal transfer, another fluid, i.e. the heat transfer fluid, in various embodiments, the heat recovery unit 540 may feed the heat and/or steam 534 as energy 544, via a closed loop process, to the C/C preform production process 502 for use in performing various operations in the production of the aircraft brakes.

In various embodiments, the heat recovery unit 540 may operate to utilize the heat and/or steam 534 to operate a turbine of an electric generator, thereby producing energy 542, i.e. electricity. In various embodiments, the heat recovery unit 540 may feed the energy 542, i.e. the electricity, to separator 524 in order for separator 524 to utilize the energy 542 to produce electric heat to separate the CO$_2$ 526 from the byproducts 522, which is fed into methanization reactor 510, to separate the N$_2$ 528 from the byproducts 522, which may be released into the atmosphere, and to separate the H$_2$O 530 from the byproducts 522, which may be fed into the burner/steam generator 514 along with H$_2$O 520. In various embodiments, the heat recovery unit 540 may operate to utilize the heat and/or steam 534 to operate a turbine of an electric generator, thereby producing energy 544, i.e. electricity. In various embodiments, the heat recovery unit 540 may feed the energy 544, i.e. the electricity, to the C/C preform production process 502 to utilize the energy 542 to produce electric heat in order that the C/C preform production process 502 uses the heat for performing various operations in the production of the aircraft brakes.

In various embodiments, the heat recovery unit 540 using the heat and/or steam 534 to operate a turbine of an electric generator, thereby producing energy 542, 544, i.e. electricity, any excess energy, 546, i.e. electricity, may be fed into other processes within a plant where the C/C preform production process 502 operates or sold as excess energy to an electric provider via an electric grid. In various embodiments, excess steam 548 of the heat and/or steam 534 may then be condensed to generate H$_2$O 538, which may be fed into the burner/steam generator 514 along with H$_2$O 520 and H$_2$O 530. In various embodiments, the condensing may be performed by the heat recovery unit 540 in response the heat recovery unit 540 is able to remove enough heat from the heat and/or steam 534. In various embodiments, in response the heat recovery unit 540 not being able to remove enough heat from the heat and/or steam 534, then the excess steam 548 may be fed to condenser 536. In various embodiments, the condenser 536 condenses the excess steam 548. Accordingly, system 500 provides for CO$_2$ emission recovery by converting the recovered CO$_2$ into other products that may be utilized by the C/C preform production process 502.

Figure 6:
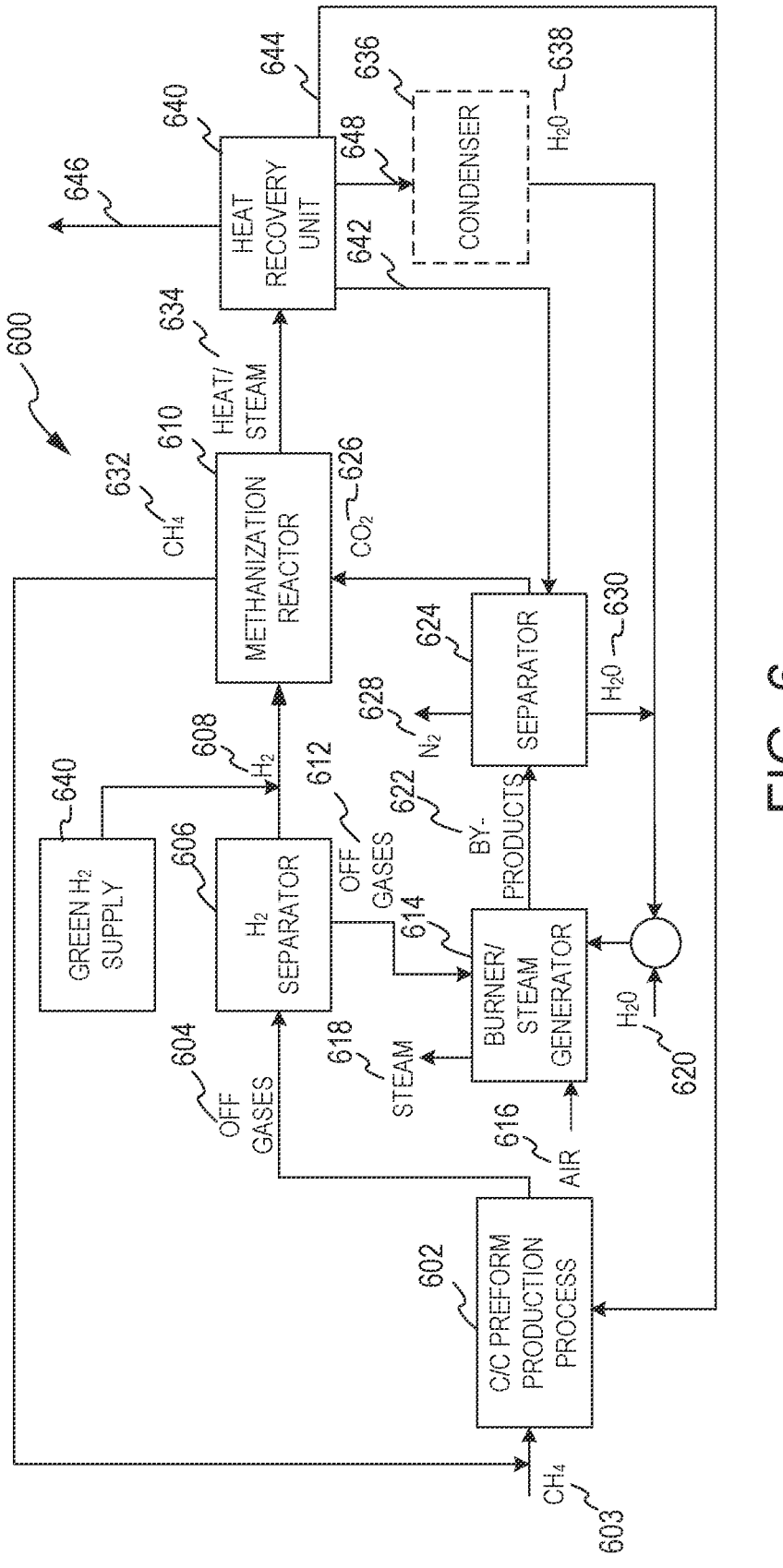
FIG. 6 illustrates a system for energy recovery of converting recovered $CO_2$ into other products, in accordance with various embodiments.

Referring now to FIG. 6, in accordance with various embodiments, a system 600 for energy recovery of converting recovered CO$_2$ into other products is illustrated. In various embodiments, the C/C preform production process 602 utilizes natural gases such as methane (CH$_4$) 603 to perform various operations in the production of aircraft brakes. However, in various embodiments, during the C/C preform production process 602 various off gases 604, i.e. hydrocarbons, are produced. Accordingly, in system 600, the C/C preform production process 602 feeds the various off gases 604, i.e., hydrocarbons, CO$_2$, H$_2$, and nitrogen (N$_2$), among others, into $H_2$ separator 606. In various embodiments, $H_2$ separator 606 separates $H_2$ 608 from the various off gases 604 using one or more of membrane separation, pressure swing absorption (PSA), captured by solid sorbents, or cryogenic distillation, among others. In various embodiments, the $H_2$ separator 606 feeds the $H_2$ 608 into methanization reactor 610 and feeds the remaining off gases 612, i.e. heavier hydrocarbons, as well as $CO_2$ and $N_2$, among others, into burner/steam generator 614.

In various embodiments, the burner/steam generator 614 burns the remaining off gases 612 utilizing air 616 to generate steam 618 from incoming water ($H_2O$) 620. In various embodiments, the steam 618 may be utilized to operate other components of the C/C preform production process 602. During the operations performed by the burner/steam generator 614, in addition to generating the steam 618, the burner/steam generator 614 generates byproducts 622, such as such as $CO_2$, $H_2O$, and $N_2$, among others, which the burner/steam generator 614 feeds into separator 624. Separator 624 may operate to separate the $CO_2$ 626 from the byproducts 622, which is fed into methanization reactor 610, to separate the $N_2$ 628 from the byproducts 622, which may be released into the atmosphere, and to separate the $H_2O$ 630 from the byproducts 622, which may be fed into the burner/steam generator 614 along with $H_2O$ 620. The separator 624 may one or more of absorption, adsorption, cryogenic distillation, captured by solid sorbents or solvents such as mono-ethanol amine (MEA), or membrane separation, among others for the separation process.

In various embodiments, the methanization reactor 610 utilizes the incoming $H_2$ 608, which may be supplemented by green $H_2$ supply 640, and $CO_2$ 626 to perform a methanization process in order to produce methane ($CH_4$) 632, which is fed into the C/C preform production process 602 or another system to perform various operation in the production the aircraft brakes, such as heat generation. In various embodiments, green $H_2$ supply 640 may be $H_2$ generated sustainably via electrolysis from a green $H_2$ supply device, such as a solar generator or wind generator. In various embodiments, in the production of $CH_4$ 632, the methanization reactor 610 also produces heat and/or steam 634 in the form of a gas exhaust and/or steam exhaust, which is fed into heat recovery unit 640. In various embodiments, the heat recovery unit 640 may operate to utilize the heat and/or steam 634 to generate energy 642, i.e. heat, via thermal transfer, another fluid that, once heated, may be utilized as a heat transfer fluid. In various embodiments, the heat recovery unit 640 may feed the energy 642, i.e. the heat transfer fluid, via a closed loop process, to separator 624 in order for separator 624 to utilize the provided heat to separate the $CO_2$ 626 from the byproducts 622, which is fed into methanization reactor 610, to separate the $N_2$ 628 from the byproducts 622, which may be released into the atmosphere, and to separate the $H_2O$ 630 from the byproducts 622, which may be fed into the burner/steam generator 614 along with $H_2O$ 620. In various embodiments, the heat recovery unit 640 may operate to utilize the heat and/or steam 634 to generate energy 644, i.e. heat, via thermal transfer, another fluid that, once heated, may be utilized as a heat transfer fluid. In various embodiments, the heat recovery unit 640 may feed the energy 644, i.e. the heat transfer fluid, via a closed loop process, to the C/C preform production process 602 in order that the C/C preform production process 602 uses the heat for performing various operations in the production of the aircraft brakes.

In various embodiments, rather than using the heat and/or steam 634 to heat, via thermal transfer, another fluid, i.e. the heat transfer fluid, in various embodiments, the heat recovery unit 640 may feed the heat and/or steam 634 as energy 642, via a closed loop process, to separator 624 in order for separator 624 to separate the $CO_2$ 626 from the byproducts 622, which is fed into methanization reactor 610, to separate the $N_2$ 628 from the byproducts 622, which may be released into the atmosphere, and to separate the $H_2O$ 630 from the byproducts 622, which may be fed into the burner/steam generator 614 along with $H_2O$ 620. In various embodiments, rather than the heat recovery unit 640 using the heat and/or steam 634 to heat, via thermal transfer, another fluid, i.e. the heat transfer fluid, in various embodiments, the heat recovery unit 640 may feed the heat and/or steam 634 as energy 644, via a closed loop process, to the C/C preform production process 602 for use in performing various operations in the production of the aircraft brakes.

In various embodiments, the heat recovery unit 640 may operate to utilize the heat and/or steam 634 to operate a turbine of an electric generator, thereby producing energy 642, i.e. electricity. In various embodiments, the heat recovery unit 640 may feed the energy 642, i.e. the electricity, to separator 624 in order for separator 624 to utilize the energy 642 to produce electric heat to separate the $CO_2$ 626 from the byproducts 622, which is fed into methanization reactor 610, to separate the $N_2$ 628 from the byproducts 622, which may be released into the atmosphere, and to separate the $H_2O$ 630 from the byproducts 622, which may be fed into the burner/steam generator 614 along with $H_2O$ 620. In various embodiments, the heat recovery unit 640 may operate to utilize the heat and/or steam 634 to operate a turbine of an electric generator, thereby producing energy 644, i.e. electricity. In various embodiments, the heat recovery unit 640 may feed the energy 644, i.e. the electricity, to the C/C preform production process 602 to utilize the energy 642 to produce electric heat in order that the C/C preform production process 602 uses the heat for performing various operations in the production of the aircraft brakes.

In various embodiments, the heat recovery unit 640 using the heat and/or steam 634 to operate a turbine of an electric generator, thereby producing energy 642, 644, i.e. electricity, any excess energy, 646, i.e. electricity, may be fed into other processes within a plant where the C/C preform production process 602 operates or sold as excess energy to an electric provider via an electric grid. In various embodiments, excess steam 648 of the heat and/or steam 634 may then be condensed to generate $H_2O$ 638, which may be fed into the burner/steam generator 614 along with $H_2O$ 620 and $H_2O$ 630. In various embodiment the condensing may be performed by the heat recovery unit 640 in response the heat recovery unit 640 is able to remove enough heat from the heat and/or steam 634. In various embodiments, in response the heat recovery unit 640 not being able to remove enough heat from the heat and/or steam 634, then the excess steam 648 may be fed to condenser 636. In various embodiments, the condenser 636 condenses the excess steam 648. Accordingly, system 600 provides for $CO_2$ emission recovery by converting the recovered $CO_2$ into other products that may be utilized by the C/C preform production process 602.

Referring now to FIG. 7, in accordance with various embodiments, a method for energy recovery of converting recovered $CO_2$ into other products is illustrated. For ease of description, the method 700 is described with reference to FIGS. 4 thru 6. At block 702, a heat recovery unit receives at least one of heat or steam from a methanization reactor operating to convert carbon dioxide ($CO_2$) and supplied hydrogen ($H_2$) via methanization to produce methane ($CH_4$). At block 704, the heat recovery unit generates energy using at least one of the heat or the steam from the methanization reactor. At block 706, the heat recovery unit supplies the generated energy to at least one of a carbon/carbon (C/C) preform production process, a separator, or another system.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Numbers, percentages, or other values stated herein are intended to include that value, and also other values that are about or approximately equal to the stated value, as would be appreciated by one of ordinary skill in the art encompassed by various embodiments of the present disclosure. A stated value should therefore be interpreted broadly enough to encompass values that are at least close enough to the stated value to perform a desired function or achieve a desired result. The stated values include at least the variation to be expected in a suitable industrial process, and may include values that are within 10%, within 6%, within 1%, within 0.1%, or within 0.01% of a stated value. Additionally, the terms "substantially," "about," or "approximately" as used herein represent an amount close to the stated amount that still performs a desired function or achieves a desired result. For example, the term "substantially," "about," or "approximately" may refer to an amount that is within 10% of, within 6% of, within 1% of, within 0.1% of, and within 0.01% of a stated amount or value.

Furthermore, no element, component, or method step in the present disclosure is intended to be dedicated to the public regardless of whether the element, component, or method step is explicitly recited in the claims. No claim element herein is to be construed under the provisions of 36

U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above-described concepts can be used alone or in combination with any or all of the other above-described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A system for thermal energy recovery, the system comprising:
   a heat recovery unit;
   a carbon/carbon (C/C) preform production process unit configured to perform a carbon/carbon (C/C) preform production process which generates off gases;
   a separator; and
   a methanization reactor operating to convert carbon dioxide ($CO_2$) and supplied hydrogen ($H_2$) via methanization to produce methane ($CH_4$),
   wherein the heat recovery unit is configured to:
      receive at least one of heat or steam from the methanization reactor;
      recover thermal energy using at least one of the heat or the steam from the methanization reactor; and
      supply the thermal energy to the carbon/carbon (C/C) preform production process and the separator,
      wherein the separator is configured to utilize the heat to separate the $CO_2$ from the off gases and is configured to provide the $CO_2$ to the methanization reactor; and
      wherein the methanization reactor is configured to feed the $CH_4$ into the into the C/C preform production process.

2. The system of claim 1, further comprising:
   a heat transfer fluid, wherein the heat recovery unit is configured to utilize at least one of the heat or the steam to heat the heat transfer fluid and wherein the heat transfer fluid is configured to transfer heat to at least one of the C/C preform production process or the separator.

3. The system of claim 2,
   wherein the C/C preform production process is configured to utilize the heat to produce an aircraft brake and, in the process, is configured to generate various off gases from which the supplied $H_2$ is separated.

4. The system of claim 2, wherein the separator is further configured to separate nitrogen ($N_2$) from the byproducts and release the $N_2$ into an atmosphere.

5. The system of claim 2, wherein the separator is further configured to separate water ($H_2O$) from the byproducts and feeds the $H_2O$ into the burner/steam generator.

6. The system of claim 1, wherein the heat recovery unit is configured to utilize the steam to transfer heat to at least one of the C/C preform production process or the separator.

7. The system of claim 1, further comprising:
   a turbine, wherein the heat recovery unit is configured to utilize the at least one of the heat or the steam to operate the turbine to produce electricity and wherein the electricity is either utilized to generate heat in at least one of the C/C preform production process, the separator, or the other system or utilized as direct power for operations to power equipment or processes.

8. The system of claim 1, further comprising:

a burner/steam generator, wherein, in generating the thermal energy using the steam from the methanization reactor, the heat recovery unit is configured to condense excess steam to water ($H_2O$) which is configured to be supplied to the burner/steam generator.

9. The system of claim 1, further comprising:

a burner/steam generator; and a condenser, wherein, in generating the thermal energy using the steam from the methanization reactor, the heat recovery unit is configured to provide excess steam to the condenser and wherein the condenser is configured to condense the steam to water ($H_2O$) which is configured to be supplied to the burner/steam generator.

10. A method for thermal energy recovery, the method comprising:

receiving, by a heat recovery unit, at least one of heat or steam from a methanization reactor operating to convert carbon dioxide ($CO_2$) and supplied hydrogen ($H_2$) via methanization to produce methane ($CH_4$);

recovering, by the heat recovery unit, thermal energy using at least one of the heat or the steam from the methanization reactor; and supplying, by the heat recovery unit, the thermal energy to a carbon/carbon (C/C) preform production process and a separator, wherein the separator utilizes the thermal energy to separate the $CO_2$ from off gases generated by the carbon/carbon (C/C) preform production process and provide the $CO_2$ to the methanization reactor to perform a methanization process in order to produce $CH_4$, which is fed into the C/C preform production process.

11. The method of claim 10, wherein the heat recovery unit uses at least one of the heat or the steam to heat a heat transfer fluid and wherein the heat transfer fluid transfers heat to at least one of the C/C preform production process or the separator.

12. The method of claim 11, wherein the C/C preform production process utilizes the heat to produce an aircraft brake and, in the process, generate various off gases from which the supplied $H_2$ is separated.

13. The method of claim 11, wherein the separator separates nitrogen ($N_2$) from the byproducts and release the $N_2$ into an atmosphere.

14. The method of claim 11, wherein the separator further separates water ($H_2O$) from the byproducts and feeds the $H_2O$ into the burner/steam generator.

15. The method of claim 10, wherein the heat recovery unit uses the steam to transfer heat to at least one of the C/C preform production process or the separator.

16. The method of claim 10, wherein the heat recovery unit uses the at least one of the heat or the steam to operate a turbine to produce electricity and wherein the electricity is either utilized to generate heat in at least one of the C/C preform production process, the separator, or the other system or utilized as direct power for operations to power equipment or processes.

17. The method of claim 10, wherein, in generating the thermal energy using the steam from the methanization reactor, the heat recovery unit condenses excess steam to water ($H_2O$) which is supplied to a burner/steam generator.

18. The method of claim 10, wherein, in generating the thermal energy using the steam from the methanization reactor, the heat recovery unit provides excess steam to a condenser and wherein the condenser condenses the steam to water ($H_2O$) which is supplied to a burner/steam generator.

* * * * *